United States Patent [19]
Horn

[11] Patent Number: 4,739,756
[45] Date of Patent: Apr. 26, 1988

[54] ENDOTRACHEAL TUBE

[76] Inventor: Sherman W. Horn, 6346 Valley Trail, Dimondale, Mich. 48821

[21] Appl. No.: 943,718

[22] Filed: Dec. 19, 1986

[51] Int. Cl.⁴ .................. A61M 16/00; A62B 9/06; A62B 9/02
[52] U.S. Cl. .................. 128/207.14; 128/207.15; 128/207.16
[58] Field of Search .................. 128/207.15, 207.14, 128/207.16; 604/283, 175, 97

[56] References Cited

U.S. PATENT DOCUMENTS

| | | | |
|---|---|---|---|
| 565,386 | 8/1896 | Meengs | 604/97 |
| 3,173,418 | 3/1965 | Baran | 128/207.15 |
| 4,022,219 | 5/1977 | Basta | 128/207.14 |
| 4,143,658 | 3/1979 | Rambosek et al. | 128/203.15 |
| 4,327,720 | 5/1982 | Bronson et al. | 128/207.15 |
| 4,327,721 | 5/1982 | Goldin et al. | 128/207.15 |
| 4,334,534 | 6/1982 | Ozaki | 128/207.15 |
| 4,378,796 | 4/1983 | Milhaud | 128/207.15 |
| 4,417,576 | 11/1983 | Baran | 128/207.15 |
| 4,453,545 | 6/1984 | Inoue | 128/207.15 |
| 4,584,998 | 4/1986 | McGrail | 128/604 |
| 4,669,463 | 6/1987 | McConnell | 604/283 |

Primary Examiner—William E. Kamm
Assistant Examiner—George Manuel
Attorney, Agent, or Firm—R. Martin Oliveras

[57] ABSTRACT

An endotracheal tube comprises: a main flexible hollow tube member including an annular wall for forming a large central lumen for the input transport of oxygen and for the output transport of the products of respiration or of suctioning; a small lateral lumen being located in such hollow tube member annular wall for the input transport of medication to be delivered distally to the internal lining of the lungs; and an ejection ring being located at the most distal annular surface of such hollow tube member annular wall, such ejection ring including a rear input channel for receiving the medication from such small lateral lumen, and including a plurality of uniformly spaced apart front output openings or orifices for ejecting such medication as a spray distally.

12 Claims, 4 Drawing Sheets

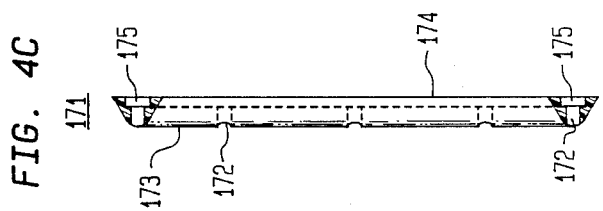
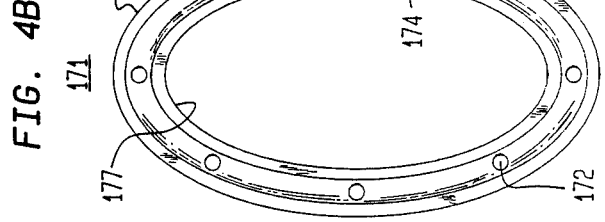
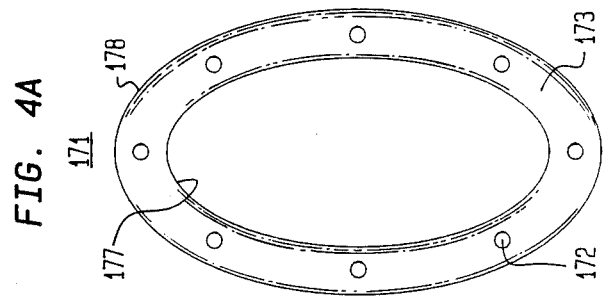

ENDOTRACHEAL TUBE

FIELD OF THE INVENTION

This invention relates to medical devices and in particular to an improved endotracheal tube which includes additional means for the distal delivery of medication to the internal lining of the lungs.

DISCUSSION OF THE PRIOR ART

The prior art reveals several endotracheal tube embodiments as follows:

(a) Baran U.S. Pat. No. 3,173,418 entitled "Double Wall Endotracheal Cuff" discloses an endotracheal cuff comprising a tubular base member, an imperforate inflatable tubular inner cuff member, a distensible outer cuff member, and passage means communicating with the space between the cuff members for introducing anesthetic into the space and transmission of such anesthetic outwardly through the perforations in the wall of the outer cuff member;

(b) Basta U.S. Pat. No. 4,022,219 entitled "Endotracheal Device" discloses an endotracheal tube comprising a tubular member including a tapered distal end and two lumen, and an adaptor for allowing transport of oxygen along the second lumen and for allowing transport of aspirated fluids along the first lumen;

(c) Rambosek et al U.S. Pat. No. 4,143,658 entitled "Intratracheal Injection System For Animals" discloses a catheter needle, and a needle fitting through such catheter;

(d) Bronson et al U.S. Pat. No. 4,327,720 entitled "Esophageal Endotracheal Airway" discloses a tubular airway device comprising: a larger diameter, shorter flexible tube; a smaller diameter, longer flexible tube; an inflatable and deflatable balloon; and a second inflatable and deflatable tubular balloon;

(e) Goldin U.S. Pat. No. 4,327,721 entitled "Endotracheal Tube With Topical Agent Delivery System And Method Of Using Same" discloses a medical device comprising a flexible insertion tube, spraying means, first lumen means, an expansible cuff member, and second lumen means;

(f) Osaki U.S. Pat. No. 4,334,534 entitled "Emergency Airway Management Device" discloses an airway device comprising an outer tube, an inner tube, interior sealing means, exterior sealing means, and a pilot balloon;

(g) Inoue U.S. Pat. No. 4,453,545 entitled "Endotracheal Tube With Movable Endobronchial Blocker For One Lug Anesthesia" discloses an apparatus comprising an elongated endotracheal tube, a first inflatable cuff, and an endobronchial blocker;

(h) Baran U.S. Pat. No. 4,417,576 entitled "Double Wall Surgical Cuff" discloses a surgical cuff comprising a tubular base member, an imperforate flexible inflatable tubular inner cuff member, a flexible distensible tubular outer cuff member, a sponge-like material, first passage means, and second passage means; and (i) McGrail U.S. Pat. No. 4,584,998 entitled "Multipurpose Tracheal Tube" discloses a balloon-type catheter comprising an extruded tube and an inflatable balloon.

It therefore appears that the Improved Endotracheal Tube of the present invention is not disclosed by such prior art endotracheal tube embodiments.

Objects of the present invention are therefore:

(a) to provide the ability to give a patient who needs an endotracheal tube certain medication without the need for an intravenous line;

(b) to provide an improved endotracheal tube which allows for the distal delivery of medication to the internal lining of the lungs while at the same time allowing for the inlet of oxygen and the outlet of the products of respiration or of suctioning; and (c) to provide an improved endotracheal tube which allows for the distal delivery of medication to the internal lining of the lungs especially for such emergency conditions as status asthmaticus.

SUMMARY AND FEATURES OF THE PRESENT INVENTION

A summary and features of the present invention are that:

(a) according to the present invention, an improved endotracheal tube comprises: a main flexible hollow tube member including an annular wall for forming a first large central lumen for the input transport of oxygen and for the output transport of the products of respiration or of suctioning; a second small lateral lumen being located in such hollow tube member annular wall for the input transport of medication to be delivered distally to the internal lining of the lungs; and an ejection ring being located at the most distal annular surface of such hollow tube member annular wall, such ejection ring including a rear input channel for receiving the medication from such second small lateral lumen, and including a plurality of uniformly spaced apart front output openings or orifices for ejecting such medication as a spray distally;

(b) the ratio of the diameter of such distal ejection ring front output openings relative to the outer diameter of such hollow tube member is about 0.02 to 0.06;

(c) the ratio of the diameter of such distal ejection ring front output openings relative to the radial thickness of such hollow tube member annular wall is about 0.1 to 0.3;

(d) the range as to the optimum number of such distal ejection ring front output openings is about 4 to 10;

(e) in a first configuration, such distal ejection ring is an annular ellipse and is adapted to fit onto the slanted most distal annular surface of such hollow tube member annular wall;

(f) the ratio of the radial thickness of such distal ejection ring relative to the outer diameter of such hollow tube member is about 0.08;

(g) the ratio of the radial thickness of such distal ejection ring rear input channel relative to the outer diameter of such hollow tube member is about 0.04;

(h) the ratio of the longitudinal height of such distal ejection ring front output openings relative to the outer diameter of such hollow tube member is about 0.04;

(i) the ratio of the longitudinal height of such distal ejection ring rear input channel relative to the outer diameter of such hollow tube member is about 0.04;

(j) the ratio of the diameter of such annular wall small lateral lumen relative to the outer diameter of such hollow tube member is about 0.08;

(k) the angle between the line perpendicular to such most distal annular wall surface containing such distal ejection ring relative to the longitudinal axis of such hollow tube member may be about 0 to 30 degrees;

(l) the ratio of the diameter of such distal ejection ring front output openings or orifices increases as the outer diameter of such hollow tube member increases;

(m) the ratio of the radial thickness of such hollow tube member annular wall increases as the outer diameter of such hollow tube member increases; and (n) the number of such distal ejection ring front output openings or orifices decreases as the outer diameter of such hollow tube member decreases.

Advantages of the present invention are therefore that:

(a) it allows for the distal delivery of such medication to the internal lining of the lungs without the need to cease ventilation via the endotracheal tube;

(b) it allows for such medication to reach the internal lining of the lungs in a more efficient and uniform spray;

(c) it allows for ventilating and medicating of the patient simultaneously and more rapidly; and (d) it allows for delivery of such medication to the internal lining of the lungs of the patient without the need to disconnect the endotracheal tube from the ventilatory source.

DESCRIPTION OF THE DRAWING

The above and other objects, features, and advantages of the present invention will be better appreciated from a reading of the following detailed description in conjunction with the drawing in which:

FIG. 4A is a top view of the distal ejection ring at the distal ejection port of such improved endotracheal tube; FIG. 4B is a bottom view of such distal ejection ring; and FIG. 4C is a cross-sectional side view along the major diameter of such distal ejection ring;

DETAILED DESCRIPTION OF THE PRESENT INVENTION

Figure 1:
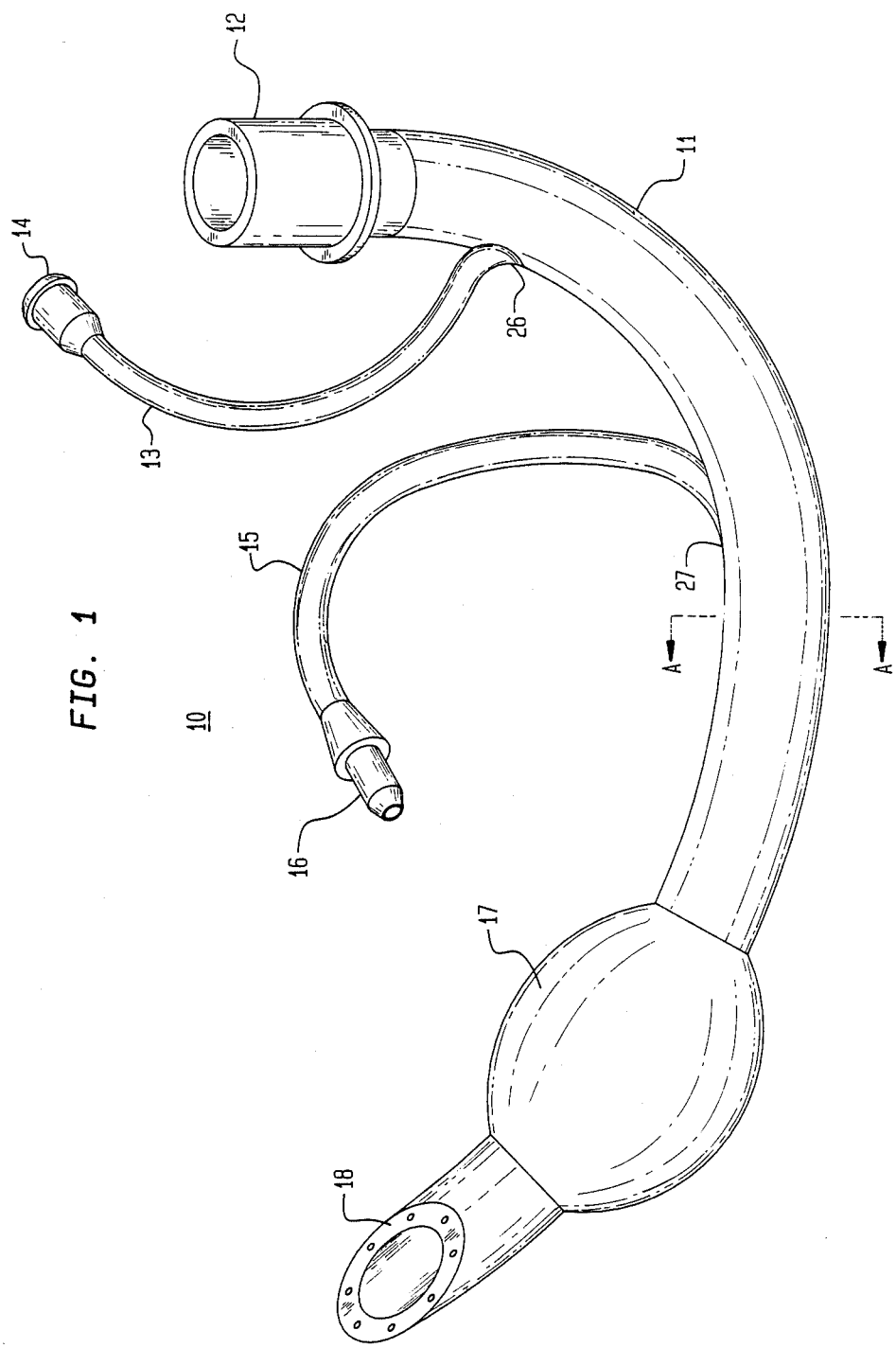
FIG. 1 is a perspective view of the improved endotracheal tube of the present invention.

FIG. 1 is a perspective view of improved endotracheal tube 10 of the present invention comprising: proximal medication injection port 14; flexible hollow tube 13 for transpoting such medication from proximal medication injection port 14 to location 26 of a first lateral passageway or lumen being located within the annular wall of main flexible hollow tube member 11; proximal primary air supply or oxygen input port 12 for providing such primary air supply input to the main air supply lumen or passageway of main flexible hollow tube member 11; proximal secondary air injection port 16; flexible hollow tube 15 for transporting such secondary air input to location 27 of a second lateral passageway or lumen also being located within the annular wall of main flexible hollow tube member 11; distal external inflatable balloon 17 being located exterior to the outer annular wall surface of main flexible hollow tube member 11 and being responsive to such secondary air input from proximal secondary air injection port 16; and distal combined primary air supply and medication ejection port 18 being jointly responsive to proximal primary air supply input port 12 and to proximal medication injection port 14. Proximal secondary air injection port 16, flexible hollow tube 15, proximal medication injection port 14, flexible hollow tube 13, and proximal primary air supply input port 12 are located outside the mouth of the patient; that portion of the main air supply lumen of main flexible hollow tube member 11 distal to location 27 and that portion of the main air supply lumen of main flexible hollow tube member 11 proximal to distal external inflatable balloon 17 are located deep within the mouth or within the proximal trachea of the patient; and distal external inflatable balloon 17 and distal ejection port 18 are located at least as far as the proximal tracheal of the patient. Distal external inflatable balloon 17 is inflated in response to such secondary air input being provided via proximal secondary air injection port 16, flexible hollow tube 15, and such second lateral lumen or passageway being located within the annular wall of main flexible hollow tube member 11 whereby the external surface of distal external inflatable balloon 17 seals off at the trachea the passage of gases or fluids from or to the lungs except as allowed by the main air supply lumen of improved endotracheal tube 10.

Figure 2:
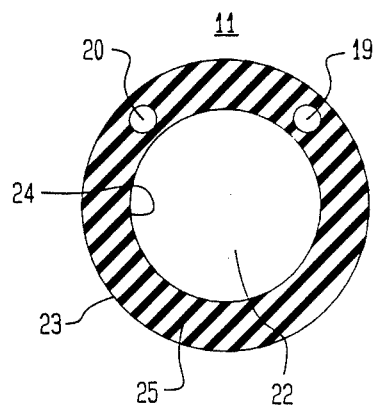
FIG. 2 is a cross-sectional longitudinal view of the hollow tube member of such improved endotracheal tube.

FIG. 2 is a cross-sectional longitudinal view along line A—A of main flexible hollow tube member 11 of improved endotracheal tube 10 showing: main air supply passageway or lumen 22; annular wall 25 including internal surface 24 and external surface 23; first lateral lumen or passageway 20 being located within annular wall 25 and being adapted to carry medication from location 26 of flexible hollow tube 13 to distal ejection port 18; and second lateral lumen or passageway 19 also being located within annular wall 25 and being adapted to carry air from location 27 of flexible hollow tube 15 to distal external inflatable balloon 17. Main flexible hollow tube member 11 including annular wall 25 and first and second lateral lumens or passageways 20 and 19 are made using known techniques. Main flexible hollow tube member 11 is defined to have an inner diameter D1, an outer diameter D2, and an annular wall radial thickness D2–D1. First lateral lumen 20 is defined to have a diameter D3 and second lateral lumen 19 is defined to have a diameter D4.

Figure 3B:
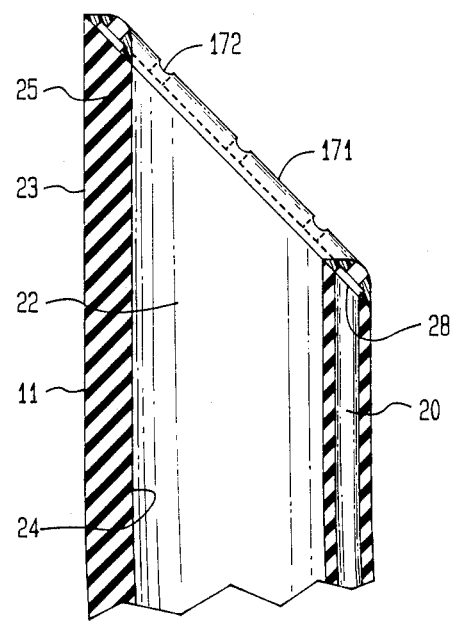
FIG. 3B is a cross-sectional side view along the longitudinal axis of such distal ejection port.
Figure 3A:
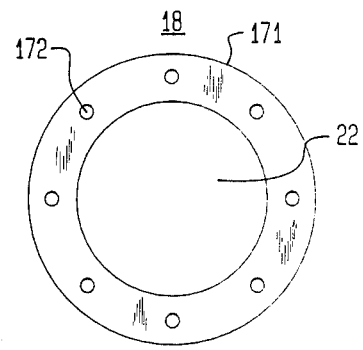
FIG. 3A is an end view of the distal ejection port of such improved endotracheal tube.

FIG. 3A is an end view of distal ejection port 18 along the longitudinal axis of improved endotracheal tube 10 showing: main air supply lumen or passageway 22 of main flexible hollow tube member 11; and distal ejection ring 171 including a plurality of uniformly spaced apart output openings or orifices 172. Ejection ring 171 is adapted to fit just distal to the most distal annular surface of annular wall 25 and is adapted to receive the medication being brought forward along first lateral lumen or passageway 20.

FIG. 3B is a cross-sectional side view along the longitudinal axis of distal ejection port 18 of improved endotracheal tube 10 showing: main flexible hollow tube member 11 including annular wall 25, internal surface 24, external surface 23, main air supply lumen or passageway 22, and first lateral lumen or passageway 20; and ejection ring 171 including output openings or orifices 172 wherein the most distal end of first lateral lumen or passageway 20 is adapted to communicate with an input channel or opening being located at the rear of ejection ring 171 at location 28. In this configuration, the line perpendicular to ejection ring 171 and the most distal annular surface of annular wall 25 are slanted at an angle of about 0 to 30 degrees relative to the longitudinal axis of main flexible hollow tube member 11.

FIG. 4A is a top view of distal ejection ring 171 along the line perpendicular to the most distal annular surface of annular wall 25 showing: inner radial edge 177, outer radial edge 178, top convex surface 173, and output openings or orifices 172. The ratio of the diameter D5 of such output openings or orifices 172 relative to the outer diameter D2 of main flexible hollow tube member 11 is about 0.02 to 0.06 and the ratio of the diameter D5 of such output openings or orifices 172 relative to the radial thickness D2-D1 of annular wall 25 is about 0.1 to 0.3. The range as to the optimum number # of such output openings or orifices is about 4 to 10. In this configuration, distal ejection ring 171 is an annular ellipse and is adapted to fit onto the most distal annular surface of annular wall 25 wherein the line perpendicular to distal ejection ring 171 and such most distal annular surface of annular wall 25 is slanted at an angle of about 0 to 30 degrees relative to the longitudinal axis of main flexible hollow tube member 11. In such configuration where the line perpendicular to the most distal annular surface of annular wall 25 and distal ejection ring 171 is parallel to the longitudinal axis of main flexible hollow tube member 11, then distal ejection ring 171 and the most distal annular surface of annular wall 25 would be circular. The ratio of the radial thickness T1 of distal ejection ring 171 relative to the outer diameter D2 of main flexible hollow tube member 11 is about 0.08.

FIG. 4B is a bottom view of distal ejection ring 171 showing: rear annular surfaces 174; rear input channel or cutout 175 being adapted to receive such medication being delivered by first lateral pasasgeway or lumen 20 of annular wall 25 at location 28; inner radial edge 177; outer radial edge 178; and output orifices or openings 172. Rear input channel 175 is adapted to communicate internally within ejection ring 171 with output orifices or openings 172. The ratio of the radial thickness T2 of rear input channel 175 relative to the outer diameter D2 of main flexible hollow tube member 11 is about 0.04.

FIG. 4C is a cross-sectional side view along the major diameter of distal ejection ring 171 showing: rear annular surfaces 174; front convex surface 173; rear input channel 175; and output openings or orifices 172. The ratio of the longitudinal height H1 of output openings or orifices 172 relative to the outer diameter D2 of main flexible hollow tube member 11 is about 0.04 while the ratio of the longitudinal height H2 of rear input channel 175 relative to the outer diameter D2 of main flexible hollow tube member 11 is about 0.04.

Figure 5:
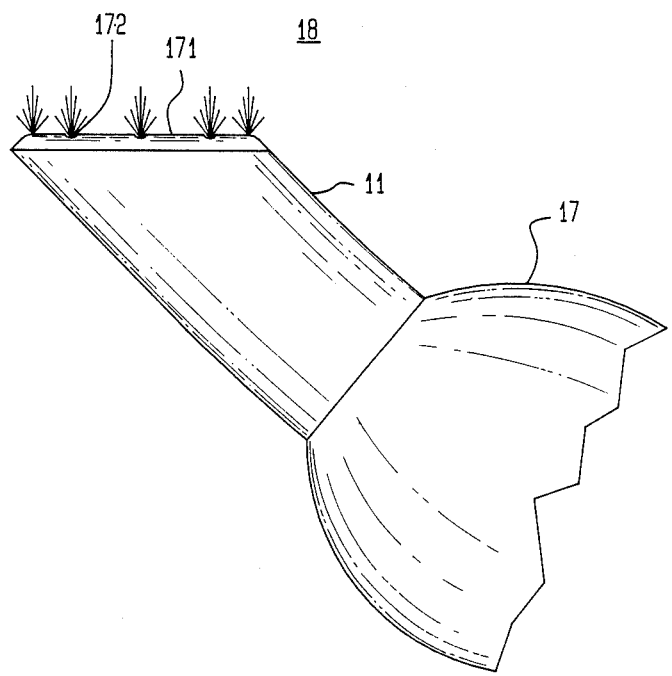
FIG. 5 is a side view of the distal ejection port of such improved endotracheal tube while in operation.

FIG. 5 is a side view of distal ejection port 18 of improved endotracheal tube 10 while in operation showing: the most distal portion of main flexible hollow tube member 11; distal inflatable external balloon 17 in the inflated configuration; and distal ejection ring 171 including output orifices or openings 172 wherein medication is exiting openings or orifices 172 in the spray form.

Figure 6:
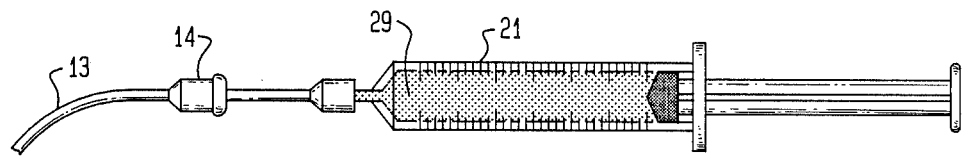
FIG. 6 is a side view of the proximal medication injection port of such improved endotracheal tube showing the attached medication containing syringe.

FIG. 6 is a side view of proximal medication injection port 14 of improved endotracheal tube 10 showing: flexible hollow tube 13; and syringe 21 including medication 29 to be forced into medication injection port 14.

The cited ratios and values relating to parameters D1, D2, D3, T1, T2, H1, and H2 are based on physiological measurements and a balance between the optimal flow of air or oxygen through main air supply passageway or lumen 22 to maintain respiration and the optimal flow of medication through rear input channel 175 and output openings or orifices 172 to alleviate the emergency condition.

While the arrangement according to the present invention has been described in terms of a specific illustrative embodiment, it will be apparent to those skilled in the art that many modifications are possible within the spirit and scope of the disclosed principle.

What is claimed is:

1. An improved endotracheal tube comprising: a main flexible hollow tube member including an annular wall for forming a large central lumen for the input transport of oxygen and for the output transport of the products of respiration or of suctioning, said annular wall including a most distal annular surface; a small lateral lumen being located in said hollow tube member annular wall for the input transport of medication to be delivered distally; and an ejection ring being located at said most distal annular surface of said hollow tube member annular wall, said distal ejection ring including a rear input channel for receiving such medication from said small lateral lumen, and including a plurality of uniformly spaced apart from output openings or orifices for ejecting such medication as a spray distally.

2. The improved endotracheal tube of claim 1 wherein: the ratio of the diameter of said distal ejection ring front output openings relative to the outer diameter of said hollow tube member is about 0.02 to 0.06.

3. The improved endotracheal tube of claim 1 wherein: the ratio of the diameter of said distal ejection ring front output openings relative to the radial thickness of said hollow tube member annular wall is about 0.1 to 0.3.

4. The improved endotracheal tube of claim 1 wherein: the range as to the optimum number of said distal ejection ring front output openings is about 4 to 10.

5. The improved endotrachreal tube of claim 1 wherein: a first configuration, said hollow tube member annular wall includes a slanted most distal annular surface, and said distal ejection ring is an annular ellipse in shape and is adapted to fit onto said slanted most distal annular surface of said hollow tube member annular wall.

6. The improved endotracheal tube of claim 1 wherein: the ratio of the radial thickness of said distal ejection ring relative to the outer diameter of said hollow tube member is about 0.08.

7. The improved endotracheal tube of claim 1 wherein: the ratio of the radial thickness of said distal ejection ring rear input channel relative to the outer diameter of said hollow tube member is about 0.04.

8. The improved endotracheal tube of claim 1 wherein: the ratio of the longitudinal height of said distal ejection ring front output openings relative to the outer diameter of said hollow tube member is about 0.04.

9. The improved endotracheal tube of claim 1 wherein: the ratio of the longitudinal height of said distal ejection ring rear input channel relative to the outer diameter of said hollow tube member is about 0.04.

10. The improved endotracheal tube of claim 1 wherein: the ratio of the diameter of said annular wall small lateral lumen relative to the outer diameter of said hollow tube member is about 0.08.

11. The improved endotracheal tube of claim 1 wherein: the angle between the line perpendicular to said annular wall most distal surface containing said distal ejection ring relative to the longitudinal axis of said hollow tube member is about 0 to 30 degrees.

12. The improved endotracheal tube of claim 1 further comprising: a second small lateral lumen also being located in said hollow tube member annular wall; and an external inflatable balloon being located proximal to said distal ejection ring for receiving air from said second small lateral lumen.

* * * * *